(12) United States Patent
Sakyu et al.

(10) Patent No.: US 8,115,037 B2
(45) Date of Patent: Feb. 14, 2012

(54) METHOD FOR PRODUCING 1,3,3,3-TETRAFLUOROPROPENE

(75) Inventors: Fuyuhiko Sakyu, Iruma-gun (JP); Yasuo Hibino, Shiki (JP)

(73) Assignee: Central Glass Company, Limited, Ube-shi (JP)

( * ) Notice: Subject to any disclaimer, the term of this patent is extended or adjusted under 35 U.S.C. 154(b) by 375 days.

(21) Appl. No.: 12/334,157

(22) Filed: Dec. 12, 2008

(65) Prior Publication Data

US 2009/0099395 A1     Apr. 16, 2009

Related U.S. Application Data

(63) Continuation-in-part of application No. PCT/JP2007/061741, filed on Jun. 11, 2007.

(30) Foreign Application Priority Data

Jun. 13, 2006  (JP) .................................. 2006-163485

(51) Int. Cl.
*C07C 17/25* (2006.01)
(52) U.S. Cl. ..................................................... 570/156
(58) Field of Classification Search ........................ None
See application file for complete search history.

(56) References Cited

U.S. PATENT DOCUMENTS

| 2,480,560 A | 8/1949 | Downing et al. |
| 5,986,151 A * | 11/1999 | Van Der Puy ................. 570/175 |
| 6,124,510 A | 9/2000 | Elsheikh et al. |

FOREIGN PATENT DOCUMENTS

| JP | 9-67281 A | 3/1997 |
| JP | 11-140002 A | 5/1999 |
| JP | 2000-63300 A | 2/2000 |
| WO | WO 2004/096737 A2 | 11/2004 |
| WO | WO 2005/019142 A1 | 3/2005 |
| WO | WO 2006/043946 A1 | 4/2006 |

OTHER PUBLICATIONS

Haszeldine, R. N. et al., "The Addition of Free Radicals to Unsaturated Systems. Part II*. Radical Addition to Olefins of the Type R•CH:CH$_2$.", J. Chem. Soc., 1953, pp. 1199-1206; CA 48 5787f.
Knunyants, I. L, et al., Izvest. Akad. Nauk S. S. S. R., Otdel. Khim. Nauk., 1960, pp. 1412-1418; CA 55, 349f.
International Search Report dated Sep. 11, 2007 including English translation of the relevant portion (Eight (8) pages).
European Search Report dated Apr. 8, 2011 (five (5) pages).

* cited by examiner

*Primary Examiner* — Sudhakar Katakam
(74) *Attorney, Agent, or Firm* — Crowell & Moring LLP

(57) ABSTRACT

There is provided a method for producing 1,3,3,3-tetrafluoropropene. This method includes dehydrofluorinating 1,1,1,3,3-pentafluoropropane in gas phase in the presence of a zirconium compound-carried catalyst in which a zirconium compound is carried on a metal oxide or activated carbon.

9 Claims, No Drawings

METHOD FOR PRODUCING 1,3,3,3-TETRAFLUOROPROPENE

TECHNICAL FIELD

The present invention relates to a method for producing 1,3,3,3-tetrafluoropropene, which is useful as an intermediate raw material of medicines, agricultural chemicals and functional materials or a refrigerant, a molten magnesium/magnesium alloy production, fire suppressing, protecting gas, and the like.

BACKGROUND OF THE INVENTION

As a method for producing 1,3,3,3-tetrafluoropropene, hitherto, there have been known a method (Non-patent Publication 1) in which 1,3,3,3-tetrafluoro-1-iodopropane is subjected to dehydroiodination by alcoholic potassium hydroxide, or a method (Non-patent Publication 2) in which 1,1,1,3,3-pentafluoropropane is subjected to dehydrofluorination by potassium hydroxide in dibutyl ether, and the like. Furthermore, a method in which 1,1,1,3,3-pentafluoropropane is subjected to dehydrofluorination with a chromium/activated carbon catalyst is disclosed in Patent Publication 1, and a method for obtaining 1,3,3,3-tetrafluoropropene from 1,1,1,3,3-pentafluoropropane by contact with a chromium-based catalyst is disclosed in Patent Publication 2.

On the other hand, as examples of dehydrofluorination reaction in gas phase in general fluoroalkane compounds, a method in which 1,1,1,3,3,3-hexafluoropropane is turned into a gaseous condition, followed by contact with activated carbon or chromium oxide catalyst to produce the corresponding propene is disclosed in Patent Publication 3, and a method in which fluoroethane is pyrolyzed by contact with activated carbon is disclosed in Patent Publication 4.

Patent Publication 1: Japanese Patent Application Publication 11-140002

Patent Publication 2: Japanese Patent Application Publication 2000-63300

Patent Publication 3: Japanese Patent Application Publication 9-67281

Patent Publication 4: U.S. Pat. No. 2,480,560 specification

Non-patent Publication 1: R. N. Haszeldine et al., J. Chem. Soc. 1953, 1199-1206; CA 48 5787f Non-patent Publication 2: I. L. Knunyants et al., Izvest. Akad. Nauk S. S. S. R., Otdel. Khim. Nauk. 1960, 1412-18; CA 55, 349f

SUMMARY OF THE INVENTION

The method of conducting a dehydrohalogenation by potassium hydroxide, such as the above Non-patent Publication 1 and Non-patent Publication 2, is a method superior in conversion and selectivity. There have been, however, many difficulties for industrial application due to that the use of solvent is necessary, that potassium hydroxide is necessary in more than stoichiometric amount, that a potassium salt resulting from the reaction becomes a lot, and the like.

Furthermore, even though the reaction conditions are severe in the dehydrofluorination reaction of a fluoroalkane compound in gas phase, conversion has not been so high in general. For example, the method of Patent Publication 3 is a method conducted by activated carbon or a chromium oxide catalyst after turning 1,1,1,3,3,3-hexafluoropropane into gas condition. Although selectivity is almost quantitative, conversion has been about 4%-50%.

<Patent Publication 3>

[Chemical Formula 1]

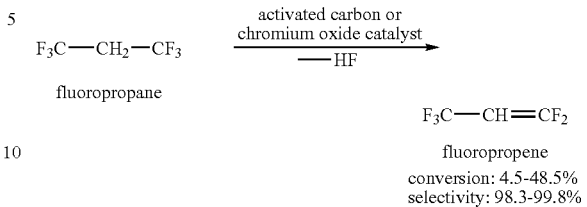

fluoropropane $F_3C-CH=CF_2$ fluoropropene conversion: 4.5-48.5%
selectivity: 98.3-99.8%

Although pyrolysis is conducted at a considerably high temperature of about 750-900° C. in Patent Publication 4, conversion is also about 40% even in this method.

<Patent Publication 4>

[Chemical Formula 2]

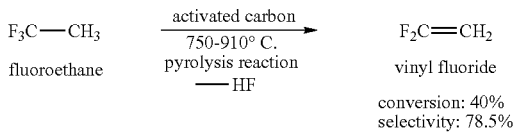

fluoroethane $F_2C=CH_2$ vinyl fluoride conversion: 40%
selectivity: 78.5%

In dehydrofluorination like the above, it is necessary to make the reaction conditions more severe to improve conversion. Furthermore, since it is also a high-temperature reaction, it is expected that industrial production is forced into a considerable difficulty, such as conversion into tar and carbonization of the product, durability of reactor, etc.

Due to these, there has been a considerable difficulty with respect to the method for producing 1,3,3,3-tetrafluoropropene, which is the target product of the present invention. Therefore, there has been a demand for establishing the production method for efficiently obtaining the target product with high yield in industrial scale.

By an eager study to solve the above task, the present inventors have found that it is particularly preferable to use a zirconium series compound as a catalyst in a method for producing 1,3,3,3-tetrafluoropropene by subjecting 1,1,1,3,3-pentafluoropropane to dehydrofluorination reaction in gas phase, thereby reaching the present invention.

Herein, the present invention is characterized in using as a catalyst a zirconium compound, that is, a zirconium compound-carried catalyst, in which a zirconium compound is carried on a metal oxide or activated carbon, or zirconia. Although it was possible to obtain 1,3,3,3-tetrafluoropropene, which was the target product, with high selectivity, in the case of using a catalyst carrying another metal without carrying a zirconium compound, conversion was very low similar to conventional techniques (see the after-mentioned Comparative Example 1-8).

However, when the present inventors used a zirconium compound-carried catalyst or zirconia as a catalyst, we obtained findings that are very efficient in industrial scale production and advantageous in practical use to obtain the target product with high selectivity and high conversion even compared with Comparative Examples (see the after-mentioned Examples 1-3).

Although details are mentioned hereinafter, the present inventors obtained findings to further suppress the production of by-products by suitably adjusting the reaction conditions.

There is a characteristic in that, although they are in small amounts, by-products having boiling points close to that of the target compound are produced by a chromium series catalyst to increase the load of distillation purification, but there are almost no by-products found by the zirconium series catalyst, thereby making the load of distillation purification small. It is assumed that this is due to easiness of the production of by-products, as isomerization and disproportionation reaction activities, etc. are known in the chromium series catalyst.

Thus, as compared with conventional liquid-phase reaction and gas-phase reaction, it became possible by using a zirconium compound-carried catalyst or zirconia to produce the target compound with a yield higher than those of conventional techniques. It is a greatly superior method with no load on productivity.

According to the present invention, there is provided a method for producing 1,3,3,3-tetrafluoropropene by subjecting 1,1,1,3,3-pentafluoropropane to a dehydrofluorination reaction in gas phase in the presence of a catalyst, the method for producing 1,3,3,3-tetrafluoropropene being characterized in that there is used a zirconium compound-carried catalyst in which a zirconium compound is carried on a metal oxide or activated carbon.

DETAILED DESCRIPTION

According to the present invention, it is possible to obtain 1,3,3,3-tetrafluoropropene with high yield and high selectivity under mild conditions by conducting the reaction using 1,1,1,3,3-pentafluoropropane as the raw material and a zirconium compound-carried catalyst or zirconia as the catalyst. Furthermore, it is also useful as an industrial production method, since 1,3,3,3-tetrafluoropropene can continuously be produced.

1,3,3,3-tetrafluoropropene is useful as an intermediate raw material of agricultural chemicals and functional materials, propellant, a protective gas of magnesium production, a foaming agent, aerosol, or refrigerant, etc.

1,1,1,3,3-pentafluoropropane (HFC-245fa), which is the raw material used in the present invention, is a substance that is easily available, since it is industrially produced as a foaming agent of hard polyurethane foams.

Thus, according to the present invention, it is possible to provide a method for producing 1,3,3,3-tetrafluoropropene by using a raw material that is available in industrial scale or is a substance that can relatively easily be produced from a raw material that is available in industrial scale.

A zirconium series catalyst according to the present invention is a zirconium compound-carried catalyst, in which a zirconium compound is carried on a metal oxide or activated carbon, or zirconia. The zirconium compound used upon preparing the zirconium compound-carried catalyst is, for example, at least one selected from the group consisting of oxides, fluorides, chlorides, fluorochlorides, oxyfluorides, oxychlorides, oxyfluorochlorides of zirconium.

The metal oxide useful as the carrier is, for example, at least one selected from the group consisting of alumina, zirconia, titania, and magnesia. Activated carbon useful as another carrier may be used by selecting from various commercial ones. For example, it is possible to cite an activated carbon produced from bituminous coal (CALGON GRANULAR ACTIVATED CARBON CAL (made by TOYO CALGON CO.), coconut husk coal (for example, made by Takeda Pharmaceutical Company Limited), etc. Of course, it is not limited to these kinds and producers.

The method for preparing a zirconium compound-carried catalyst according to the present invention is not limited. It can be prepared by impregnating or spraying a metal oxide, activated carbon, or a compound prepared by previously subjecting them to a halogen modification treatment with hydrogen fluoride, hydrogen chloride, a chlorofluorohydrocarbon, etc., which is used as the carrier, with a solution prepared by dissolving a soluble compound of zirconium.

It is suitable that the amount of the zirconium compound carried is 0.1-80 wt %, preferably 1-40 wt %, in percentage amounting to the total amount with the carrier. As the soluble compound of zirconium to be carried on the carrier, it is possible to cite nitrates, phosphates, chlorides, oxides, oxychlorides, and oxyfluorides of the relevant metal that are soluble in a solvent such as water, hydrochloric acid, aqueous ammonia, ethanol, acetone, and the like.

As the metal compound to be carried, besides zirconium, it is possible to carry a metal compound of at least one selected from chromium, titanium, aluminum, manganese, nickel, cobalt, iron, molybdenum, niobium, tantalum, iridium, tin, hafnium, and vanadium to be coexistent with zirconium.

It is effective to previously treat the catalyst made to carry the metal by any method, with a fluorination agent, such as hydrogen fluoride and a fluorohydrocarbon, at a temperature higher than a predetermined reaction temperature, prior to use, to activate the catalyst. In the activation of the catalyst, it is also possible to use a fluorinating method after a previous treatment with a chlorohydrocarbon. Furthermore, it is an effective means to supply the reactor during the reaction with oxygen, chlorine, a fluorinated or chlorinated hydrocarbon, etc. in order to prolong the catalyst lifetime and to improve conversion and reaction yield.

The reaction temperature is 200-600° C., preferably 200-500° C., more preferably 200° C.-400° C. If the reaction temperature is lower than 200° C., the reaction is slow and is not practical. If the reaction temperature exceeds 600° C., the catalyst lifetime becomes short. Furthermore, although the reaction proceeds rapidly, the decomposition products and the like are produced, thereby lowering selectivity of 1,3,3,3-tetrafluoropropene. Therefore, it is not preferable.

Furthermore, in the present invention, besides the target product 1,3,3,3-tetrafluoropropene, due to the progress of a further dehydrofluorination of this, the resulting 3,3,3-trifluoropropyne was produced in some cases as a by-product.

(Scheme 1)

[Chemical Formula 3]

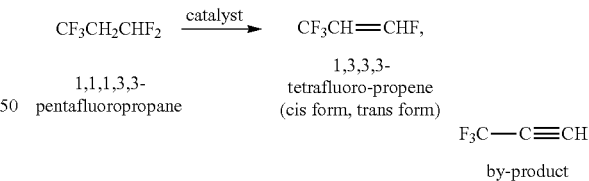

The present inventors have found that it is possible to further suppress the production of 3,3,3-trifluoropropyne by conducting at the above reaction temperature. For example, in Examples 1-3, it is one of particularly preferable embodiments to adjust the reaction temperature to 300-350° C.

In the method of the present invention, it is optional to supply an inert gas, such as nitrogen, helium and argon, simultaneously with 1,1,1,3,3-pentafluoropropane that is supplied to the reaction region. Furthermore, it is optional to make hydrogen fluoride coexistent.

Although the reaction pressure is not particularly limited, it is preferable to conduct that at 0.1-10 kg/cm² from the aspect of apparatus. It is desirable to select a condition in which the raw material organic matter and hydrogen fluoride that exist in the system do not become liquid in the reaction system. The contact time is normally 0.1-300 seconds, preferably 5-200 seconds.

It suffices that the reactor used in the present invention is made of a material having heat resistance and corrosion resistance against hydrogen fluoride, hydrogen chloride, etc., preferably stainless steel, Hastelloy, Monel, platinum, etc. Furthermore, it can also be made by a material lined with these metals.

A product containing 1,3,3,3-tetrafluoropropene flowing out of the reactor after the treatment by the method of the present invention turns into a finished product through purification by a known method. The purification method is not limited. For example, it can be conducted firstly by washing the product, from which hydrogen fluoride to be recovered has previously been separated by sulfuric acid or the like, with water or an alkali aqueous solution to remove acidic substances, such as hydrogen chloride and hydrogen fluoride, followed by drying and distillation to remove organic impurities. Hydrogen fluoride absorbed into sulfuric acid or the like can be recovered by distillation and can be reused.

Furthermore, the separated organic impurities can be recovered and can be reintroduced into the reactor. For example, it is possible to recover the unreacted 1,1,1,3,3-pentafluoropropane containing 1,3,3,3-tetrafluoropropene and obtained by the above-mentioned distillation and to reuse it as the starting raw material of the present invention. As shown in the after-mentioned Example 5, in the case of using a low-purity 1,1,1,3,3-pentafluoropropane containing 1,3,3,3-tetrafluoropropene in cis form as the starting raw material of the reaction, the reaction proceeds with much higher conversion and much higher selectivity to obtain 1,3,3,3-tetrafluoropropene, as compared with those of Comparative Examples.

In the following, the present invention is explained in more detail by examples, but it is not limited to these embodiments. Herein, "%" of the compositional analysis value represents "areal %" of the composition obtained by measuring the reaction mixture directly by gas chromatography (unless particularly described, the detector is FID).

EXAMPLES

Preparation Example 1

4.5 g of a special grade reagent $ZrOCl_2 \cdot 8H_2O$ was dissolved in ethanol. In this solution, 50 mL of spherical alumina having a diameter of 5 mm was immersed, followed by standing still for a whole day and night. Then, the solvent was distilled off, followed by drying at 150° C. under reduced pressure. The obtained zirconium-carried alumina was placed into a cylindrical reaction tube that was equipped with an electric furnace, had a diameter of 2 cm and a length of 40 cm, and was made of SUS316. The temperature was increased to 200° C., while nitrogen gas was allowed to flow. At the time when no water outflow was found, nitrogen gas was accompanied with hydrogen fluoride, and its concentration was gradually increased. When hot spot due to fluorination of the placed zirconium compound-carried alumina reached an outlet end of the reaction tube, the reactor temperature was increased to 450° C. That condition was maintained for 1 hour to prepare the catalyst.

Preparation Example 2

In a solution prepared by dissolving 3.3 g of a special grade reagent $ZrOCl_2 \cdot 8H_2O$ in ethanol, 50 mL of a granular activated carbon (Takeda Pharmaceutical Company Limited, GRANULAR SHIRO SAGI GX) having a diameter of 4-6 mm was immersed, followed by standing still for a whole day and night. Then, the solvent was distilled off, followed by drying at 150° C. under reduced pressure. The obtained zirconium compound-carried, activated carbon was placed into a cylindrical reaction tube that was equipped with an electric furnace, had a diameter of 2 cm and a length of 40 cm, and was made of SUS316. The temperature was increased to 200° C., while nitrogen gas was allowed to flow. At the time when no water outflow was found, nitrogen gas was accompanied with hydrogen fluoride, and its concentration was gradually increased. The reactor temperature was increased to 450° C., and that condition was maintained for 1 hour to prepare the catalyst.

Preparation Example 3

Catalysts were prepared under the same conditions as those of Preparation Example 2, except in that special grade reagents $MoCl_5$, $TiCl_4$, $IrCl_4$ and $SnCl_4$ were used, and they were dissolved in ethanol or water to make solutions.

Example 1

40 mL of the catalyst prepared by Preparation Example 1 as catalyst was placed at around the center of a gas-phase reaction apparatus (made of SUS316, diameter: 2 cm, length: 40 cm) formed of a cylindrical reaction tube to be heated by an outside heating apparatus. While nitrogen gas was allowed to flow at a flow rate of about 200 ml/minute, the temperature of the reaction tube was increased to 300° C., and it was continued to introduce hydrogen fluoride at a rate of about 0.2 g/minute for 1 hour. The introduction of hydrogen fluoride and nitrogen gas was stopped, and it was started to supply the previously vaporized 1,1,1,3,3-pentafluoropropane as the raw material organic matter to the reactor at a rate of 0.15 g/minute.

One hour after the start of the reaction, the reaction became stable. Therefore, the produced gas discharging from the reactor was bubbled into water to remove acidic gas, followed by collecting with a dry ice/acetone trap. The collected organic matter was analyzed by gas chromatography, and the results are shown in Table 1.

Example 2

40 mL of the catalyst prepared by Preparation Example 2 as catalyst was placed at around the center of a gas-phase reaction apparatus (made by SUS316, diameter: 2 cm, length: 40 cm) formed of a cylindrical reaction tube to be heated by an outside heating apparatus. While nitrogen gas was allowed to flow at a flow rate of about 200 ml/minute, the temperature of the reaction tube was increased to 400° C., and it was continued to introduce hydrogen fluoride at a rate of about 0.2 g/minute for 1 hour. The temperature of the reaction tube was decreased to 350° C. The introduction of hydrogen fluoride and nitrogen gas was stopped, and it was started to supply the previously vaporized 1,1,1,3,3-pentafluoropropane as the raw material organic matter to the reactor at a rate of 0.15 g/minute. The results are shown in Table 1.

Example 3

40 mL of a zirconia formed into a columnar form of 3×6 mm was placed into a gas-phase reaction apparatus (made by SUS316, diameter: 2 cm, length: 40 cm) formed of a cylindrical reaction tube to be heated by an outside heating apparatus. While nitrogen gas was allowed to flow at a flow rate of about 400 ml/minute, the temperature of the reaction tube was increased to 400° C., and it was continued to introduce hydrogen fluoride at a rate of about 0.2 g/minute for 1 hour. The temperature of the reaction tube was decreased to 350° C. The introduction of hydrogen fluoride and nitrogen gas was stopped, and it was started to supply the previously vaporized 1,1,1,3,3-pentafluoropropane as the raw material organic matter to the reactor at a rate of 0.15 g/minute. The results are shown in Table 1.

Example 4

50 mL of the catalyst prepared by Preparation Example 1 as catalyst was placed at around the center of a gas-phase reaction apparatus (made by SUS316, diameter: 2 cm, length: 40 cm) formed of a cylindrical reaction tube to be heated by an outside heating apparatus. While nitrogen gas was allowed to flow at a flow rate of about 200 ml/minute, the temperature of the reaction tube was increased to 400° C., and it was continued to introduce hydrogen fluoride at a rate of about 0.2 g/minute for 1 hour. The temperature of the reaction tube was decreased to 350° C. The introduction of hydrogen fluoride and nitrogen gas was stopped, and it was started to supply the previously vaporized 1,1,1,3,3-pentafluoropropane as the raw material organic matter to the reactor at a rate of 1.40 g/minute. The results are shown in Table 1.

Thus, in Examples 1-4, it is possible to obtain the target product with a higher conversion and a higher selectivity as compared with Comparative Examples by using the zirconium compound-carried catalyst in which a zirconium compound is carried on a metal oxide or activated carbon.

Example 5

50 mL of the catalyst prepared by Preparation Example 1 as catalyst was placed at around the center of a gas-phase reaction apparatus (made by SUS316, diameter: 2 cm, length: 40 cm) formed of a cylindrical reaction tube to be heated by an outside heating apparatus. While nitrogen gas was allowed to flow at a flow rate of about 200 ml/minute, the temperature of the reaction tube was increased to 400° C., and it was continued to introduce hydrogen fluoride at a rate of about 0.2 g/minute for 1 hour. The temperature of the reaction tube was decreased to 350° C. The introduction of hydrogen fluoride and nitrogen gas was stopped, and it was started to supply a previously vaporized 1,1,1,3,3-pentafluoropropane (raw material composition: 74.9%) containing 1,3,3,3-tetrafluoropropene (cis) (raw material composition: 25%) as the raw material organic matter to the reactor at a rate of 1.40 g/minute. The results are shown in Table 2.

TABLE 1

Raw Material Purity: 99.9%

| | PFP Supply Rate g/min | Reaction Temp. ° C. | Product Composition (%) | | | | Conversion*[1] | Selectivity*[2] |
|---|---|---|---|---|---|---|---|---|
| | | | PFP | TeFP(t) | TeFP(c) | TFPy | | |
| Example 1 | 0.15 | 300 | 5.88 | 75.48 | 17.70 | 0.47 | 94.02 | 99.11 |
| Example 2 | 0.15 | 350 | 15.08 | 68.69 | 16.01 | 0.00 | 84.82 | 99.85 |
| Example 3 | 0.15 | 350 | 8.73 | 74.98 | 15.29 | 0.12 | 91.17 | 99.02 |
| Example 4 | 1.40 | 350 | 16.69 | 70.12 | 13.03 | 0.03 | 83.21 | 99.93 |
| Com. Ex. 1 | 0.15 | 300 | 59.16 | 33.71 | 7.14 | 0.00 | 40.74 | 100 |
| Com. Ex. 2 | 0.15 | 350 | 41.83 | 47.31 | 10.70 | 0.00 | 58.07 | 99.91 |
| Com. Ex. 3 | 0.15 | 300 | 87.28 | 10.05 | 2.53 | 0.01 | 12.61 | 99.72 |
| Com. Ex. 4 | 0.15 | 350 | 54.30 | 36.78 | 8.64 | 0.00 | 45.59 | 99.61 |
| Com. Ex. 5 | 0.15 | 300 | 73.96 | 21.61 | 4.33 | 0.00 | 25.94 | 100 |
| Com. Ex. 6 | 0.15 | 350 | 52.48 | 39.33 | 7.98 | 0.00 | 47.41 | 99.77 |
| Com. Ex. 7 | 0.15 | 300 | 88.98 | 8.53 | 2.19 | 0.00 | 10.92 | 98.17 |
| Com. Ex. 8 | 0.15 | 350 | 72.69 | 20.65 | 5.51 | 0.00 | 27.21 | 96.15 |

PFP: 1,1,1,3,3-pentafluoropropane
TeFP(t): 1,3,3,3-tetrafluoropropene (trans)
TeFP(c): 1,3,3,3-tetrafluoropropene (cis)
TFPy: 3,3,3-trifluoropropyne
*[1]Conversion (%) was calculated by (99.9% − product (%) of PFP)
*[2]Selectivity (%) was calculated by 100 × [(TeFP(t) + TeFP(c))/conversion]
*For example*)in the case of Example 1: Conversion = 99.9% − 5.88% = 94.02% Selectivity = 100 × [(75.48 + 17.70)/94.02] = 99.11%

TABLE 2

Raw Material Purity: PFP = 74.9%, TeFP(c) = 25%

| | Raw Material Supply Rate g/min | Reaction Temp. ° C. | Product Composition (%) | | | | Conversion of TeFP(t)*[1] | Selectivity of TeFP(t)*[2] |
|---|---|---|---|---|---|---|---|---|
| | | | PFP | TeFP(t) | TeFP(c) | TFPy | | |
| Example 5 | 1.40 | 350 | 13.31 | 72.38 | 14.16 | 0.03 | 72.43 | 99.93 |

PFP: 1,1,1,3,3-pentafluoropropane
TeFP(t): 1,3,3,3-tetrafluoropropene (trans)
TeFP(c): 1,3,3,3-tetrafluoropropene (cis)
TFPy: 3,3,3-trifluoropropyne
*[1]Conversion (%) of TeFP(t) was calculated by (raw material purity (%) − product (%) of PFP − TeFP(c) (%))
*[2]Selectivity (%) of TeFP(t) was calculated by 100 × (TeFP(t)/conversion)
*For example*)in the case of Example 5: Conversion = 99.9% − 13.31% − 14.16% = 72.43% Selectivity = 100 × (72.38/72.43) = 99.93%

Thus, in Example 5, even in the case of using the low-purity 1,1,1,3,3-pentafluoropropane as the starting raw material, it is possible to obtain the target product with high conversion and high selectivity similar to Examples 1-4.

Comparative Examples 1-8

The reactions were conducted in the same manner as that of Example 2, except in that the temperature of the reaction tube of 1,1,1,3,3-pentafluoropropane was each set to 300° C. or 350° C. and that the catalysts prepared by Preparation Example 3 (Comparative Examples 1-2: 5% Mo/C, Comparative Examples 3-4: 5% Ti/C, Comparative Examples 5-6: 5% Ir/C, Comparative Examples 7-8: 5% Sn/C) were used. The results are also each shown in Table 1.

In examples in which other metals are carried, selectivity is good, but conversion is considerably low. Therefore, it is necessary to make the reaction conditions severer in order to make the reaction proceed well. Thus, there is a difficulty somewhat in industrial production.

The invention claimed is:

1. A method for producing 1,3,3,3-tetrafluoropropene, comprising dehydrofluorinating 1,1,1,3,3-pentafluoropropane in gas phase in the presence of a zirconium compound-carried catalyst in which a zirconium compound is carried on a metal oxide or activated carbon.

2. A method according to claim 1, wherein the metal oxide is at least one selected from the group consisting of alumina, zirconia, titania, and magnesia.

3. A method according to claim 1, wherein the zirconium compound is at least one selected from the group consisting of fluorides, chlorides, fluorochlorides, oxyfluorides, oxychlorides, and oxyfluorochlorides of zirconium.

4. A method for producing 1,3,3,3-tetrafluoropropene, comprising dehydrofluorinating 1,1,1,3,3-pentafluoropropane in gas phase in the presence of zirconia as a catalyst at a temperature of 200° C. to 400° C.

5. A method according to claim 1, wherein a product containing 1,3,3,3-tetrafluoropropene and obtained by the dehydrofluorination is subjected to a purification by separating hydrogen fluoride from the product, followed by washing with water or an alkali aqueous solution to remove an acidic substance, then drying, and then distillation to remove an organic impurity.

6. A method according to claim 4, wherein a product containing 1,3,3,3-tetrafluoropropene and obtained by the dehydrofluorination is subjected to a purification by separating hydrogen fluoride from the product, followed by washing with water or an alkali aqueous solution to remove an acidic substance, then drying, and then distillation to remove an organic impurity.

7. A method according to claim 1, wherein the metal oxide is one subjected to a modification treatment with hydrogen fluoride, hydrogen chloride or a chlorofluorohydrocarbon.

8. A method according to claim 4, wherein the dehydrofluorinating is conducted in the presence of at least one selected from the group consisting of nitrogen, helium, argon, and hydrogen fluoride.

9. A method according to claim 1, wherein the dehydrofluorinating is conducted in the presence of at least one selected from the group consisting of nitrogen, helium, argon, and hydrogen fluoride.

* * * * *